US012609042B2

(12) United States Patent
Kim

(10) Patent No.: US 12,609,042 B2
(45) Date of Patent: Apr. 21, 2026

(54) METHOD AND SYSTEM FOR GUIDING USE OF INHALER

(71) Applicant: INTIN INC., Daegu (KR)

(72) Inventor: Ji Hoon Kim, Seoul (KR)

(73) Assignee: INTIN INC., Daegu (KR)

( * ) Notice: Subject to any disclaimer, the term of this patent is extended or adjusted under 35 U.S.C. 154(b) by 0 days.

(21) Appl. No.: 18/356,521

(22) Filed: Jul. 21, 2023

(65) Prior Publication Data

US 2023/0368686 A1 Nov. 16, 2023

Related U.S. Application Data

(63) Continuation of application No. PCT/KR2021/001143, filed on Jan. 28, 2021.

(51) Int. Cl.
G09B 5/00 (2006.01)
A61M 15/00 (2006.01)
(Continued)

(52) U.S. Cl.
CPC ............... G09B 5/00 (2013.01); A61M 15/00 (2013.01); G16H 20/10 (2018.01); G16H 40/67 (2018.01);
(Continued)

(58) Field of Classification Search
CPC ........ G09B 5/00; G09B 5/125; G09B 23/288; G09B 19/24; A61M 15/00;
(Continued)

(56) References Cited

U.S. PATENT DOCUMENTS 6,358,058 B1 * 3/2002 Strupat ............. A61M 15/0065
434/262
8,807,131 B1 * 8/2014 Tunnell ............. A61M 15/0021
128/200.14
(Continued)

FOREIGN PATENT DOCUMENTS

JP        2018-531055 A     10/2018
JP        6543240 B2      7/2019
(Continued)

OTHER PUBLICATIONS

European Search Report in EP Application No. 21923316.0 dated Feb. 13, 2024.
(Continued)

*Primary Examiner* — Jack Yip
(74) *Attorney, Agent, or Firm* — Knobbe, Martens, Olson & Bear, LLP

(57) ABSTRACT

A method and system for guiding use of an inhaler is proposed. The method may include receiving, by a user terminal, from an auxiliary terminal worn on a part of the user's body and interlocking with the user terminal, a detection value obtained by detecting a user's action including at least one of motion or sound in association with the use of the inhaler. The method may also include analyzing the detection value by the user terminal. The method may further include determining, by the user terminal, a completion status of the user's action. The method may further include outputting, by the user terminal, result information regarding a result of the user's performing an action.

18 Claims, 5 Drawing Sheets

(51) Int. Cl.
    *G16H 20/10*         (2018.01)
    *G16H 40/67*         (2018.01)

(52) U.S. Cl.
    CPC ............... *A61M 2205/3375* (2013.01); *A61M 2205/3561* (2013.01); *A61M 2205/58* (2013.01); *A61M 2230/63* (2013.01)

(58) Field of Classification Search
    CPC .. A61M 2205/3375; A61M 2205/3561; A61M 2205/58; A61M 2230/63; A61M 15/0025; A61M 15/009; A61M 2016/0018; A61M 2205/332; A61M 2205/3553; A61M 2205/3592; A61M 2205/505; A61M 2205/52; A61M 2209/088; A61M 2210/083; G16H 20/10; G16H 40/67; G16H 20/13; G16H 40/63; G06F 3/167; G04G 9/0064; G04G 21/02
    See application file for complete search history.

(56) References Cited

U.S. PATENT DOCUMENTS

| | | | | |
|---|---|---|---|---|
| 11,457,861 B1* | 10/2022 | Pratt | .................... | A61B 5/0024 |
| 2011/0253139 A1* | 10/2011 | Guthrie | ............ | A61M 15/0005 |
| | | | | 128/203.14 |
| 2013/0053719 A1* | 2/2013 | Wekell | ................ | A61M 15/008 |
| | | | | 600/538 |
| 2014/0322682 A1* | 10/2014 | Baym | ..................... | G09B 5/02 |
| | | | | 340/5.6 |
| 2016/0082208 A1* | 3/2016 | Ballam | ............. | A61M 16/0003 |
| | | | | 128/200.14 |
| 2016/0129182 A1* | 5/2016 | Schuster | ............. | A61M 15/008 |
| | | | | 702/56 |
| 2016/0144141 A1* | 5/2016 | Biswas | ............... | A61M 15/009 |
| | | | | 128/200.23 |
| 2016/0144142 A1* | 5/2016 | Baker | ................. | A61M 15/008 |
| | | | | 128/200.23 |
| 2016/0325058 A1* | 11/2016 | Samson | ............... | A61B 5/0022 |
| 2017/0169184 A1 | 6/2017 | Doswell et al. | | |
| 2018/0092595 A1* | 4/2018 | Chen | .................... | A61B 5/1123 |
| 2018/0318643 A1* | 11/2018 | Klee | ...................... | A61B 5/097 |
| 2020/0013313 A1* | 1/2020 | Von Hollen | .......... | A61M 15/00 |
| 2020/0260972 A1 | 8/2020 | Han et al. | | |
| 2022/0005573 A1* | 1/2022 | Chan | ................. | A61M 15/0065 |
| 2022/0058439 A1* | 2/2022 | Lee | ....................... | H04W 76/10 |
| 2022/0115107 A1* | 4/2022 | Gondalia | .............. | G16H 80/00 |

FOREIGN PATENT DOCUMENTS

| | | |
|---|---|---|
| KR | 10-1638408 B1 | 7/2016 |
| KR | 10-1654708 B1 | 9/2016 |
| KR | 10-2019-0115490 A | 10/2019 |
| KR | 10-2020-0113339 A | 10/2020 |
| WO | WO 2020/168138 A1 | 8/2020 |

OTHER PUBLICATIONS

International Search Report mailed Oct. 25, 2021 in International Application No. PCT/KR2021/001143.
Office Action dated Feb. 27, 2023 in Korean Application No. 10-2021-0012237.

\* cited by examiner

FIG. 4

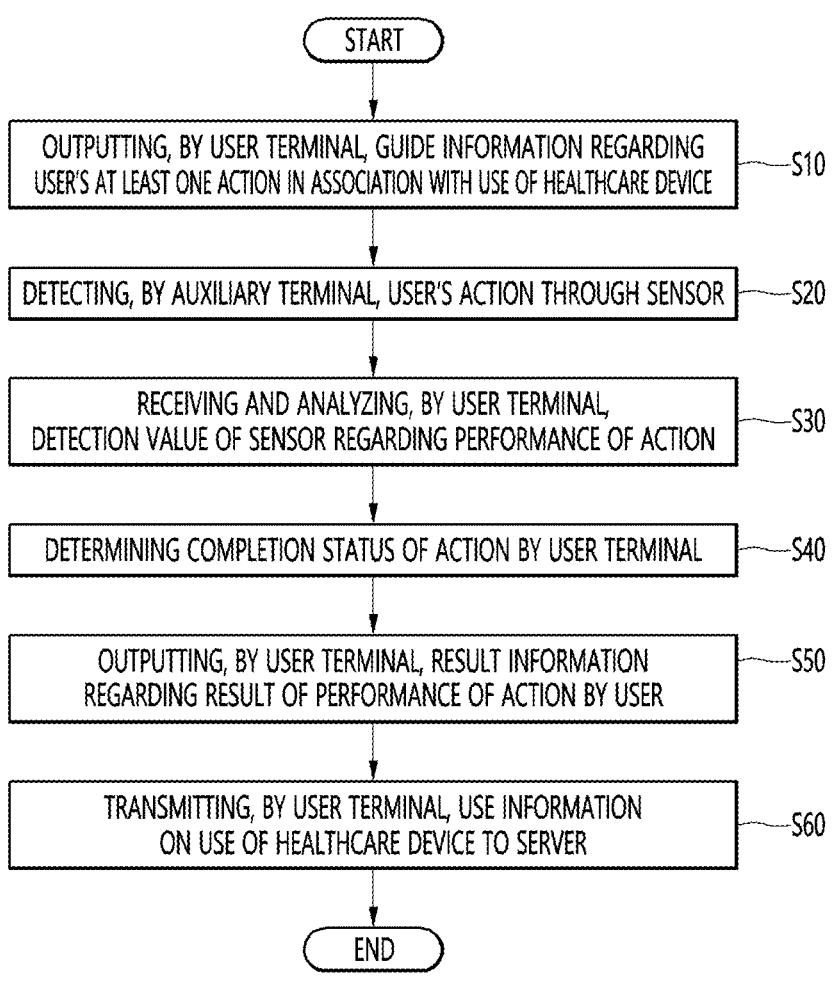

START

OUTPUTTING, BY USER TERMINAL, GUIDE INFORMATION REGARDING USER'S AT LEAST ONE ACTION IN ASSOCIATION WITH USE OF HEALTHCARE DEVICE ——S10

DETECTING, BY AUXILIARY TERMINAL, USER'S ACTION THROUGH SENSOR ——S20

RECEIVING AND ANALYZING, BY USER TERMINAL, DETECTION VALUE OF SENSOR REGARDING PERFORMANCE OF ACTION ——S30

DETERMINING COMPLETION STATUS OF ACTION BY USER TERMINAL ——S40

OUTPUTTING, BY USER TERMINAL, RESULT INFORMATION REGARDING RESULT OF PERFORMANCE OF ACTION BY USER ——S50

TRANSMITTING, BY USER TERMINAL, USE INFORMATION ON USE OF HEALTHCARE DEVICE TO SERVER ——S60

END

METHOD AND SYSTEM FOR GUIDING USE OF INHALER

CROSS REFERENCE TO RELATED APPLICATIONS

This is a continuation application of International Patent Application No. PCT/KR2021/001143 filed on Jan. 28, 2021, the content of which is incorporated herein by reference in its entirety.

BACKGROUND

Technical Field

The present disclosure relates to a method and system for guiding the use of an inhaler, and more particularly, to a method and system for guiding the use of an inhaler to guide a proper use of a healthcare device such as the inhaler and detect a user's actual use to provide the user with a feedback on a result of performance of the action.

Description of Related Technology

Asthma is an inflammatory airway disorder that causes breathing difficulties, and a chronic obstructive pulmonary disease (COPD) refers to a group of respiratory conditions characterized by abnormal inflammation in the lung due to inhalation of harmful particles or gases, thereby leading to airflow blockage, impaired lung function, and breathing difficulties.

SUMMARY

One aspect is a method and system for guiding the use of an inhaler.

Another aspect is a method and system for guiding the use of an inhaler to guide the proper use of a healthcare device such as the inhaler and detect a user's actual use to provide the user with a feedback on the result of performing the action.

Another aspect is a method for guiding use of an inhaler that includes: receiving, by a user terminal, from an auxiliary terminal worn on a part of the user's body and interlocking with the user terminal, a detection value obtained by detecting a user's action including at least one of motion and sound in association with the use of the inhaler; analyzing the detection value by the user terminal; determining, by the user terminal, a completion status of the user's action; and outputting, by the user terminal, result information regarding a result of the user's performing an action.

The method may further include, after the determining of a completion status, transmitting, by the user terminal, use information regarding the use of the inhaler to a server.

The method may further include, prior to the receiving, outputting, by the user terminal, guide information regarding the user's action associated with the use of the inhaler.

The outputting of the guide information may be performed at a predetermined time interval or when biometric information of the user received from the auxiliary terminal satisfies a predetermined criterion.

The auxiliary terminal may include an accelerometer sensor and a microphone sensor, and the auxiliary terminal may detect the user's action through at least one of the accelerometer sensor and the microphone sensor.

The user's action may include a plurality of actions; in the outputting of the guide information, guide information regarding all of the plurality of operations may be output; and in the receiving, the detection value may be received after the guide information regarding all of the plurality of operations is output, and detection values obtained by continuously detecting the plurality of actions by the auxiliary terminal may be received from the auxiliary terminal.

Some of the plurality of actions may be detected through the accelerometer sensor, and the remaining of the plurality of actions may be detected through the microphone sensor.

In the plurality of actions, an action to be detected by the accelerometer sensor and an action to be detected through the microphone sensor may be alternately repeated.

The analyzing may be performed whenever an action detected by the accelerometer sensor is completed or an action detected by the microphone sensor is completed.

The analyzing may be performed after all of the plurality of actions of the user is completed.

Another aspect is a method for guiding use of an inhaler that includes: receiving, by a user terminal, from an auxiliary terminal worn on a part of the user's body and interlocking with the user terminal, a detection value obtained by detecting a user's first action including at least one of motion and sound in association with the use of the inhaler; analyzing the first action by the user terminal; receiving, by the user terminal, from the auxiliary terminal, a detection value obtained by detecting a second action of the user performed after the first action; analyzing the second action by the user terminal; receiving, by the user terminal, from the auxiliary terminal, a detection value obtained by detecting a third action of the user performed after the second action; analyzing the third action by the user terminal; receiving, by the user terminal, from the auxiliary terminal, a detection value obtained by detecting a fourth action of the user performed after the third action; analyzing the fourth action by the user terminal; determining completion statuses of the first, second, third, and fourth operations by the user terminal; and outputting result information regarding a result of the user's performing an action, and the first action includes opening a cap of the inhaler, the second action includes the user's exhaling, the third action includes the user's holding the inhaler to mouth and pressing a button of the inhaler, and the fourth action includes the user's inhaling for a first time period with a button of the inhaler pressed and holding breath for a second time period longer than the first time period.

The method may further include, after the determining of a completion status, transmitting, by the user terminal, use information regarding the use of the inhaler to a server.

The method may further include, prior to receiving the detection value obtained by detecting the first action, outputting, by the user terminal, guide information regarding the user's action associated with the use of the inhaler.

The outputting of the guide information may be performed at a predetermined time interval or when biometric information of the user received from the auxiliary terminal satisfies a predetermined criterion.

The outputting of the guide information may be performed before the operation of receiving the detection value obtained by detecting the first action, and guide information regarding all of the first to fourth actions is output.

The outputting the guide information may include outputting a plurality of guide information; outputting of each of the plurality of guide information may be performed immediately before the receiving of the detection value obtained by detecting the first action, immediately before the receiving the detection value obtained by detecting the second action, immediately before the receiving of the detection value obtained by detecting the third action, and immediately before the receiving of the detection value obtained by detecting the fourth action; and the outputting of the plurality of guide information may involve outputting guide information regarding each of the first to fourth actions, which is required in the receiving of the respective actions.

The first time period may be determined in a range of 3 seconds to 7 seconds, and the second time period may be determined in a range of 8 seconds to 12 seconds.

The first action further may include shaking the inhaler a predetermined number of times.

In addition, the present disclosure includes a computer program for executing a method for guiding the use of an inhaler in combination with hardware.

In addition, a user terminal for guiding use of an inhaler according to an embodiment of the present disclosure includes: a memory; a processor connected to the memory and configured to execute instructions contained in the memory; an output unit configured to output information under the control of the processor; and a communication module configured to receive a detection value of a user's action associated with the use of the inhaler from an auxiliary terminal worn on a part of the user's body, and the processor is further configured to perform a control to receive a detection value of a user's first action associated with the use of the inhaler from the auxiliary terminal and analyze the detection value, perform a control to receive a detection value obtained by detecting a second action of the user performed after the first action from the auxiliary terminal and analyze the detection value; perform a control to receive a detection value obtained by detecting a third action of the user performed after the second action from the auxiliary terminal and analyze the detection value, perform a control to receive a detection value obtained by detecting a fourth action of the user performed after the third action from the auxiliary terminal and analyze the detection value; determine completion statuses of the first, second, third, and fourth actions, and perform a control to output result information regarding results of performance of the user's actions, and the first action includes opening a cap of the inhaler, the second action includes the user's exhaling, the third action includes the user's holding the inhaler to mouth and pressing a button of the inhaler, and the fourth action includes the user's inhaling for a first time period with a button of the inhaler pressed and holding breath for a second time period longer than the first time period.

Also, the user terminal may output guide information regarding the user's action before the auxiliary terminal detects the user's action.

The first operation may further include shaking the inhaler a predetermined number of times.

In the present disclosure, it is possible to detect a user's action associated with the use of a healthcare device by an auxiliary terminal, analyze the user's action by a user terminal, determine the user's action and determine a completion status thereof by the user terminal, and provide the user with a feedback on the same, thereby providing a proper use of the healthcare device.

DETAILED DESCRIPTION

FIG. 4 is a diagram for explaining a first embodiment of a method for guiding the use of an inhaler according to the present disclosure.

DETAILED DESCRIPTION

Figure 1:
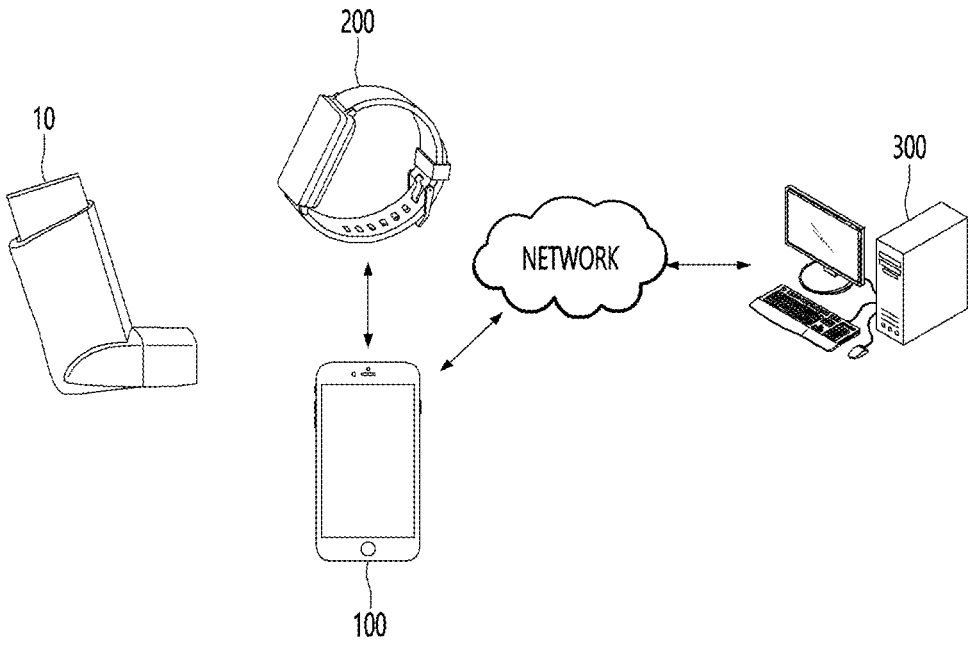
FIG. 1 is a diagram for explaining a network environment for a guide system for using a healthcare device according to an example of the present disclosure.

For treatment of patients with asthma or the COPD, medication inhalation therapy is known as the best way to deliver medication to the lung.

In detail, the medication inhalation therapy is a treatment method by which medication is administered to a patient through a dedicated inhaler, and this allows the medication to directly reach a body part requiring the medication the most, thereby maximizing the effectiveness and minimizing the potential systemic side effects of the medication.

Inhalants used for the medication inhalation therapy are classified into "controller medication", which helps continuously manage symptoms such as breathing difficulties and prevent exacerbations, and "reliever medication", which is an emergency medication to rapidly expand a narrowed airway, and the inhalants may be administered to a user through a portable asthma inhaler.

In this case, portable asthma inhalers are classified into metered dose inhalers and dry powder inhalers according to the type of inhalation container.

In particular, the metered dose inhaler are aerosol products in which medication is contained in a sealed container such as an aluminum canister and delivered by a propellant in a predetermined dose through a cartridge, and examples of the metered dose inhaler include MDIs include Rapihaler, Evohaler, and Respimat.

However, in using a portable inhaler, there are many cases where a user does not sufficiently shake medication before inhaling the medication or inhales the medication without sufficiently performing inhalation and exhalation.

In this case, there is a problem in that the effectiveness of the medication inhaled by the user through the portable inhaler is reduced and may vary by more than 30% depending on the use of the inhaler.

Hereinafter, embodiments of the present disclosure will be described in detail with reference to the accompanying drawings. In describing the present disclosure, if it is determined that a detailed description of known functions and components associated with the present disclosure unnecessarily obscure the gist of the present disclosure, the detailed description thereof will be omitted. In addition, the terms used in the specification are used to appropriately express the embodiments of the present disclosure and may be altered according to a person of a related field or conventional practice. Therefore, the terms should be defined on the basis of the entire content of this specification.

The technical terms used in the present disclosure are only for describing a special exemplary embodiment, but it is considered that the present disclosure is not limited thereto. The singular forms used in the present disclosure include plural forms as long as the phrases do not clearly have a contrary sense. The meaning of "including" used in the specification specifies a specific characteristic, area, integer, step, action, element, and/or component, but it is not considered to eliminate the existence or addition of other characteristics, areas, integers, steps, actions, elements, and/ or components.

Hereinafter, the present disclosure will be described with reference to the accompanying drawings.

FIG. 1 is a diagram for explaining a network environment for a usage guide system of a healthcare device 10 according to an example of the present disclosure.

Communication schemes for a network is not limited, and may include not only a communication scheme to utilize a telecommunication network (for example, a mobile communication network, wired Internet, wireless Internet, and a broadcast network) that the network can include, but also a short-range radio communication scheme.

As shown in FIG. 1, a system for guiding the use of the healthcare device 10 of the present disclosure includes a user terminal 100, an auxiliary terminal 200, and a server 300.

The guidance system of the present disclosure as described above may provide guidance of the use of the healthcare device 10 in associated with a user's disease.

The healthcare device 10 may include health auxiliary devices or medical devices to be used by a user in order to the treatment or healthcare of a particular condition of the user, regardless of what the condition is, and in FIG. 1, an example of a portable inhaler mainly used for asthma patients is shown.

However, the healthcare device 10 of the present disclosure is not limited to an inhaler. However, for convenience of explanation, a case where the healthcare device 10 is an inhaler will be described as an example.

The user terminal 100 may be a fixed terminal implemented as a computer device or a mobile terminal. For example, the user terminal 100 may include a smart phone, a mobile phone, a tablet PC, a computer, a laptop computer, and personal digital assistants (PDAs). For example, the user terminal 100 may communicate with the server 300 through a network using a wireless or wired communication scheme.

Such a user terminal 100 may be used by a user. The user may refer to a user of the user terminal 100 or an account registered by the server 300 as a user of a healthcare-related application. Therefore, if the server 300 transmits certain information to the user, it may mean that the information is transmitted to the user terminal 100 through the user's account registered in the server 300.

The user terminal 100 may receive and install an application associated with the use of the healthcare device 10 from the server 300 in advance. When an application associated with the use of the healthcare device 10 is installed in the user terminal 100, user information such as the user's gender, name, age, address, disease type, disease name, etc. may be input to the user terminal 100.

An operation reference value for the user's action may be input in advance in association with a disease to the user terminal 100 according to the application associated with the use of the healthcare device 10.

More specifically, when the user has an asthma-related disease, the user terminal 100 may receive, from the user, a reference operation value regarding the user's action including motion and sound through the auxiliary terminal 100 in order to preset a reference operation value for the use of the healthcare device 10, such as an inhaler, in the user terminal 100. Accordingly, the user terminal 100 may store in advance a reference operation value for a disease specified by the user.

For example, the user terminal 100 may output guide information regarding the user's action in association with the use of the healthcare device 10, the user may perform an action according to the guide information while holding the healthcare device 10 with a hand wearing the auxiliary terminal 200, the auxiliary terminal 200 may transmit to the user terminal 100 a detection value obtained by detecting the user's action, and the user terminal 100 may store the received detection value as a reference operation value.

Thereafter, when a condition for the user to use the healthcare device 10 associated with a disease is met, the user terminal 100 may output the guide information regarding the use of the healthcare device 10 to the user, analyze the user's action detected by the auxiliary terminal 200, compare the analyzed action with the reference operation value to determine whether the user's action has been performed properly, and provide the user with a feedback as result information.

In addition, the user terminal 100 may transmit use information associated with the user's usage of the healthcare device 10 to the server 300.

The configuration of the user terminal 100 will be described later with reference to FIG. 2.

The auxiliary terminal 200 may interwork with the user terminal 100 and detect the user's action.

Here, the auxiliary terminal 200 may interwork with the user terminal 100 through a network, or may interwork with the user terminal 100 through a short-range wireless communication network such as Bluetooth or Wi-Fi. In FIG. 1, a case where the auxiliary terminal 200 interworks with the user terminal 100 through a short-range wireless communication is shown as an example.

Such an auxiliary terminal 200 may be worn on a part of the user's body. For example, the auxiliary terminal 200 may include a smart watch that can be worn on a part of the user's body, such as a wrist.

Worn on a part of the body, the auxiliary terminal 200 may detect a user's action. Here, the user's action may include an action performed by a hand, which is a part of the user's body (e.g., opening the cap of the inhaler, shaking the inhaler, holding the inhaler in the mouth, pressing an inhaler button, etc.), sounds emanating from the user (e.g., sounds related to breathing-out (exhaling), breathing-in (inhaling), etc.), etc.

In addition, while worn on a part of the user's body, the auxiliary terminal 200 may detect a user's bio-signal. For example, the auxiliary terminal 200 may detect a pulse, an electrocardiogram, a body temperature, and the like as the user's bio-signals.

Such an auxiliary terminal 200 may transmit information on the user's action and information on a bio-signal to the user terminal 100.

The server 300 may receive information associated with the use of the healthcare device 10 from the user terminal 100, and store and manage the information associated with the user's usage of the healthcare device 10. For example, the server 300 may receive, from the user terminal 100, information regarding a usage time, an interval of usage, and a frequency of usage of the healthcare device 10, and may provide the user with a disease-related information through the user terminal 100 based on the received information.

Figure 2:
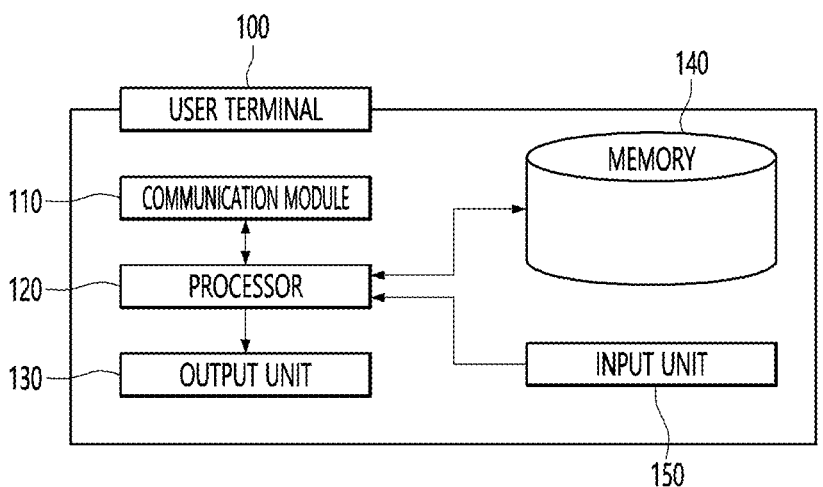
FIG. 2 is a diagram for explaining an example of a user terminal shown in FIG. 1.

FIG. 2 is a diagram for explaining an example of the user terminal 100 shown in FIG. 1.

Referring to FIG. 2, the user terminal 100 according to the embodiment may include a communication module 110, a processor 120, a memory 140, an output unit 130, and an input unit 150.

The communication module 110 may communicate with the server 300 and the auxiliary terminal 200 in a wired/wireless manner. For example, the communication module 110 may transmit or receive various types of information, data, or signals related to the use of the healthcare device 10.

The input unit 150 may receive an input of various types of information necessary for the use of the healthcare device 10. The input unit 150 may include a touch screen module, a keyboard, a mouse, buttons, a camera, a microphone, and the like.

The output unit 130 may include a display module and a speaker, and may output necessary information associated with the use of the healthcare device 10.

For example, the output unit 130 may output guide information regarding a user's action in association with the use of the healthcare device 10 as sound or image.

The output unit 130 and the input unit 150 may have an inter-layered structure or an integrated structure with the input unit 150 to implement a touch screen.

Such a touch screen may provide an input interface and an output interface between the user terminal 100 and the user.

The memory 140 serves as a storage medium, and may store a plurality of application programs or applications running on the user terminal 100, and data and commands for operations of the user terminal 100.

In one embodiment, information necessary for executing an application associated with the use of the healthcare device 10 may be stored in the memory 140 in the form of a computer program.

Such a memory 140 may be provided as any of various hardware storage devices, such as a Read-Only Memory (ROM), a Random Access Memory (RAM), an Electrically Erasable Programmable Read-Only Memory (EEPROM), a flash drive, and a hard drive, or may be provided in the form of a web storage configured to perform a storing function of the memory 130 on the Internet.

The processor 120 may control the overall operation to execute an application associated with the use of the healthcare device 10.

Figure 3:
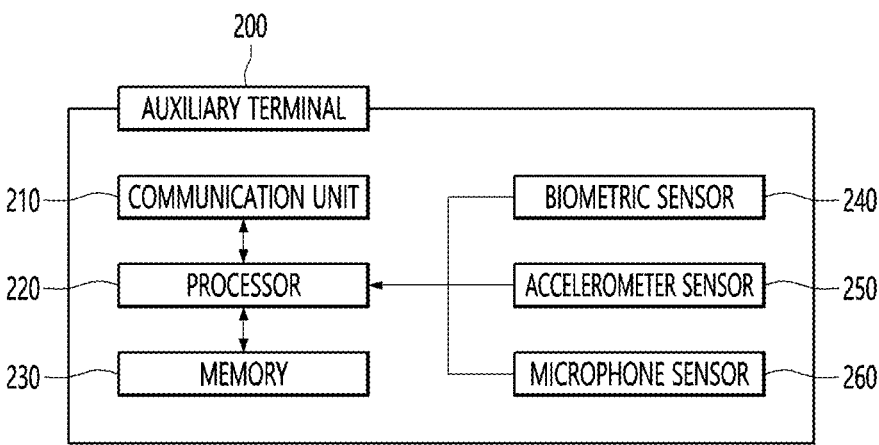
FIG. 3 is a diagram for explaining an example of an auxiliary terminal shown in FIG. 1.

FIG. 3 is a diagram for explaining an example of the auxiliary terminal 200 shown in FIG. 1.

As shown in FIG. 3, the auxiliary terminal 200 may include a communication unit 210, a processor 220, a memory 230, a biometric sensor 240, an accelerometer sensor 250, and a microphone sensor 260.

The communication unit 210 may communicate with the user terminal 100 in a wired/wireless manner.

The memory 230 serves as a storage medium and may store detection values detected by the biometric sensor 240, the accelerometer sensor 250, and the microphone sensor 260.

The processor 220 may generate detection values by processing signals detected by the biometric sensor 240, the accelerometer sensor 250, and the microphone sensor 260, and may perform a control to store the detection values in the memory 230 or to transmit the detection values to the user terminal 100 through communication unit 210.

The biometric sensor 240 may detect the user's pulse, electrocardiogram, body temperature, and the like, and the accelerometer sensor 250 may detect an amount of change in speed or the like of the auxiliary terminal 200, for example, based on the user's action such as movement of the user's arm.

The microphone sensor 260 may detect sound generated around the auxiliary terminal 200, and may detect sound such as the sound of opening of the inhaler's cap by the user to use the healthcare device 10, the sound of inhaling, the sound of exhaling, and the sound of pressing a button of the inhaler.

In addition, although not illustrated, the auxiliary terminal 200 may further include a position sensor, a geomagnetic sensor, a gyro sensor, and the like in order to more delicately detect a user's action.

FIG. 4 is a diagram for explaining a first embodiment of a method for guiding the use of the healthcare device 10 according to the present disclosure.

As shown in FIG. 4, the first embodiment of the method for guiding the use of the healthcare device 10 according to the present disclosure may include outputting guide information (S10), detecting (S20), analyzing (S30), determining (S40), outputting result information (S50), and transmitting (S60).

Here, for convenience of explanation, FIG. 4 illustrates an example in which the respective operations are sequentially performed, but the present disclosure is not necessarily limited thereto, and the order of the operations may be changed or some operations may be alternately and repeated.

In addition, in FIG. 4, the operation S10, the operation S50, and the operation S60 may be selectively included or may be omitted in some cases. However, hereinafter, for convenience of explanation, a case where the operation S10, the operation S50, and the operation S60 are included will be described as an example.

In addition, hereinafter, a case where the healthcare device 10 is the aforementioned portable inhaler will be described as an example.

In the operation S10, the user terminal 100 may output guide information regarding a user's action associated with the use of the healthcare device 10.

Here, the user terminal 100 may perform the operation S10 when the action is performed at a predetermined time interval or when the user's biometric information received from the user terminal 200 satisfies a preset criterion.

For example, the guide information may be output in the form of sound such as an alarm through the output unit 130 of the user terminal 100 at a time interval preset by the user, or may be output in the form of sound such as an alarm when the user's biometric information received from the auxiliary terminal 200 satisfies a preset criterion that indicates the user's need to use the inhaler.

In addition, after an alarm is output in the form of sound, the guide information may be output through the output unit 130 of the user terminal 100 with a combination of audio and video, showing the user's action required in association with the use of the inhaler.

In order to perform the method for guiding the use of the healthcare device 10, the user terminal 100 may perform, prior to outputting the guide information, the operation S30 of receiving and analyzing information of the biometric sensor 240 other than the accelerometer sensor 250 and the microphone sensor 260; after outputting the guide information, the user terminal 100 may receive information of the accelerometer sensor 250 and the microphone sensor 260 from the auxiliary terminal 200 in order to analyze the user's action.

In the operation S20, the auxiliary terminal 200 worn on a part of the user's body may generate a detection value obtained by detecting the user's action including motion and sound in associated with the use of the healthcare device 10.

Here, the user's action may include motion and sound, and the auxiliary terminal 200 may include the accelerometer sensor 250 and the microphone sensor 260 as described above.

In the operation S20, the auxiliary terminal 200 may be worn on a part of the user's body (e.g., a wrist) to detect the user's action through the accelerometer sensor 250, and detect sound emanating from the user through the microphone sensor 260.

When the user performs an action required in association with the use of the inhaler, the auxiliary terminal 200 may generate detection values by performing digital signal processing on signals of the user's action detected by the accelerometer sensor 250 and the microphone sensor 260. The auxiliary terminal 200 may transmit the generated detection values to the user terminal 100.

In the operation S30, the user terminal 100 may receive the detection values from the auxiliary terminal 200 and analyze the detection values. For example, in the operation S30, the user terminal 100 may analyze a detection value to visualize movement of the auxiliary terminal 200 according to the detection value or may analyze sound detected from the user.

In the operation S40, the user terminal 100 may determine a completion status of the user's action.

For example, in the operation S40, the user terminal 100 may determine a completion status of the user's action by comparing the user's action including motion and sound with a prestored reference operation value to determine a similarity therebetween.

If the determined similarity satisfies a reference value, the user terminal 100 may determine that the user's action has been completed, and if not, the user terminal 100 may determine that a required action has not been completed.

In the operation S50, the user terminal 100 may output result information regarding a result of the user's performing an action.

For example, when the user has completed a required action, sound or an image may be output indicating that the inhaler has been used according to a proper use, and when the user has not completed the required action, information on cautions and warnings regarding the use of the inhaler may be output as sound or an image.

In the operation S60, the user terminal 100 may transmit use information regarding the use of the healthcare device 10 to the server 300.

Meanwhile, the user's action required in association with the use of the healthcare device 10 may include a plurality of actions. In such a case, some operations may be alternately and repeatedly performed. This will be described with reference to FIG. 5.

Figure 5:
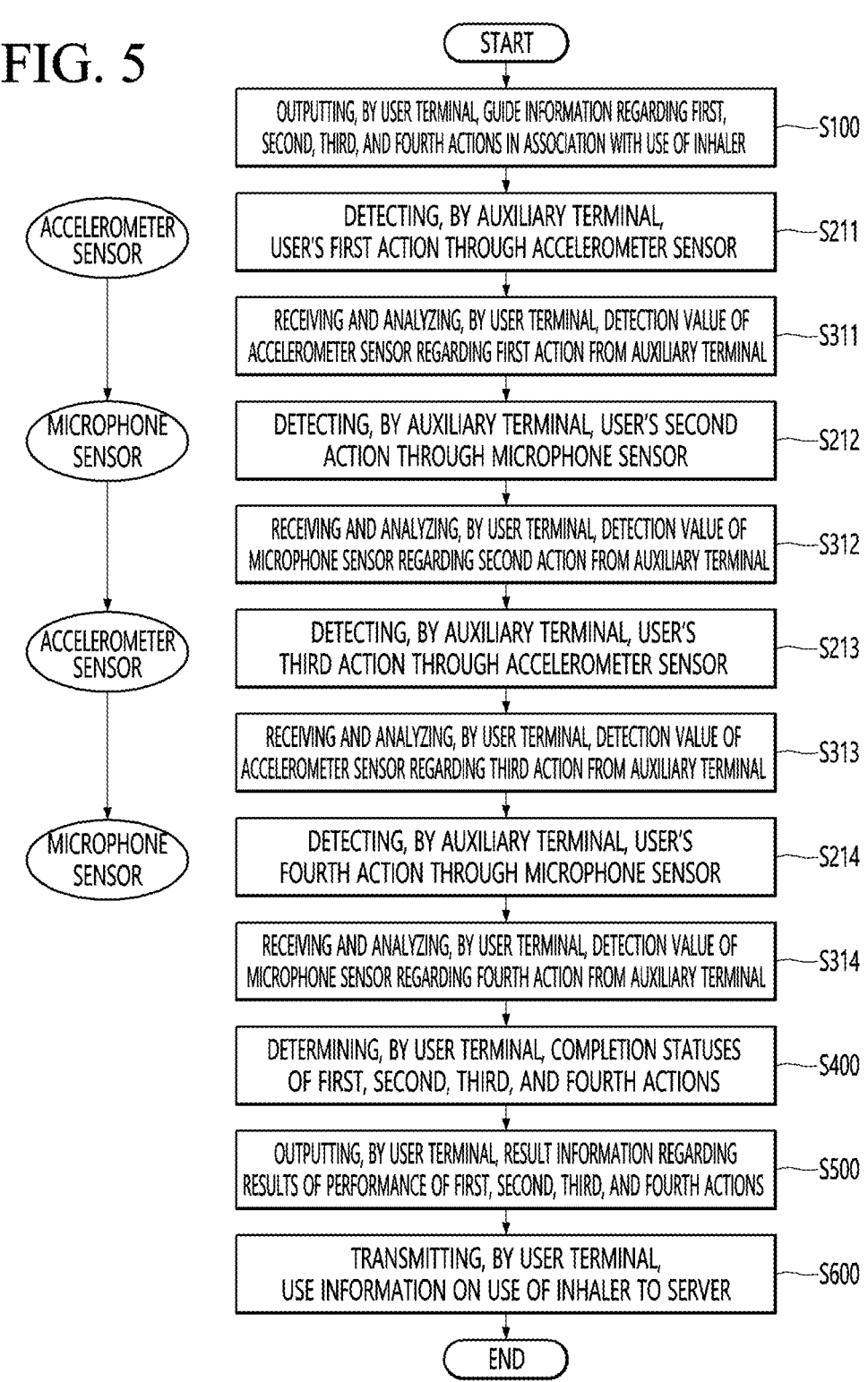
FIG. 5 is a diagram for explaining a second embodiment of a method for guiding the use of an inhaler according to the present disclosure.

FIG. 5 is a diagram for explaining a second embodiment of a method for guiding the use of the healthcare device 10 according to the present disclosure.

In the second embodiment of the method for guiding the use of the healthcare device 10 according to the present disclosure, a user's action required in association with the use of the healthcare device 10 may include a plurality of actions.

As shown in FIG. 5, the method for guiding the use of the healthcare device 10 according to the second embodiment may include: outputting guide information (S100); detecting first, second, third, and fourth actions (S211, S212, S213, and S214); analyzing the first, second, third, and fourth actions (S311, S312, S313, and S314); determining a completion status (S400); outputting result information (S500); and transmitting the result information (S600).

As in the second embodiment of the present disclosure, when the user's action required in association with the use of the healthcare device 10 includes a plurality of actions, guide information regarding all of the plurality of the first, second, third, and fourth actions may be output in the operation $100.

The operations S211, S212, S213, and S214 may be performed after guide information regarding all of the plurality of actions is output, and the auxiliary terminal 200 may continuously detect the plurality of actions.

In the operations S211, S212, S213, and S214, some of the plurality of actions may be detected by the accelerometer sensor 250, and the remaining of the plurality of actions may be detected by the microphone sensor 260. At this point, in the plurality of actions, an action to be detected by the accelerometer sensor 250 and an action to be detected by the microphone sensor 260 may be alternately and repeated.

The operations S311, S312, S313, and S314 may be performed whenever detecting an action by the accelerometer sensor 250 or detecting an action by the microphone sensor 260 is completed. However, it is also possible that the operation S30 is performed after all of the plurality of actions of the user is completed.

The respective operations in the method for guiding the use of the healthcare device 10 according to the second embodiment will be described with specific examples as follows.

For reference, an inhalant to be inhaled by the user may be contained in a liquid, gaseous, or powder form in an inhalation container attached to an inhaler.

Here, when the inhalant is contained in a liquid or gaseous form in the inhalation container, the user needs to shake the inhaler before use, and when the inhalant is contained in a powder form in the inhalation container, the user does not need to shake the inhaler before use.

As such, the method of using the inhaler may vary depending on the type of the inhalant contained in the inhalation container.

Accordingly, when the user executes an application associated with the use of the healthcare device 10 and inputs an operation value set in advance regarding the user's action required for the use of the inhaler, the user may specify which inhaler to use based on the type of inhaler and perform an action required according to guide information regarding the specified inhaler to input an operation reference value.

Here, the action input as the action reference value may include a starting action and a using action. The starting action may include an action to indicate the type of inhaler or an action related to the start of use of the inhaler separate from daily life, which is distinct from daily activities, and the using action may include first, second, third, and fourth actions associated with the use of the inhaler.

Accordingly, when using an inhaler, the user may first select an inhaler to be used through the user terminal or may start using an inhaler by performing an inhaler starting action that is distinct from daily activities. Accordingly, this may enhance the accuracy of use of an inhaler.

Hereinafter, a case where an inhaler containing a liquid or gaseous inhalant is selected by a user will be described as an example. Accordingly, the user's actions required to use the inhaler may include: a first action of opening a cap of the inhaler and shaking the inhaler 3-4 times; a second action of exhaling; a third action of holding the inhaler to the mouth and pressing a button of the inhaler to administer medication; and a fourth action of inhaling for 5 seconds with the button pressed and holding the breath for 10 seconds.

As such, when the user's actions required in association with the use of the inhaler include the first, second, third, and fourth actions, guide information regarding all of the first, second, third, and fourth actions may be output as sound or image in the operation S100.

Thereafter, the auxiliary terminal 200 may detect each action of the user and transmit a detection value to the user terminal 100.

Specifically, in the operation S211 of detecting the first action, the auxiliary terminal 200 may detect through the accelerometer sensor 250 the user's first action of opening the cap of the inhaler and shaking the inhaler 3 to 4 times, and in the operation S311, the user terminal 100 may receive a detection value of the accelerometer sensor 250 regarding the first action from the auxiliary terminal 200 and analyze the detection value.

Thereafter, in the operation S212 of detecting the second action, the auxiliary terminal 200 may detect through the microphone sensor 260 sound generated when the user performs the second action of exhaling, and in the operation S312, the user terminal 100 may receive and analyze a detection value of the microphone sensor 260 regarding the second action.

Next, in the operation S213 of detecting the third action, the auxiliary terminal 200 may detect the third action of holding the inhaler to the mouth and pressing the button of the inhaler to administer medication, and in the operation S313, the user terminal 100 may receive a detection value of the accelerometer sensor 250 regarding the third action from the auxiliary terminal 200 and analyze the detection value.

Lastly, in the operation S214 of detecting the fourth action, the auxiliary terminal 200 may detect sound generated when the fourth action of inhaling for 5 seconds with the button pressed and holding the breath for 10 seconds is performed, and in the operation S314, the user terminal 100 may receive and analyze a detection value of the microphone sensor 260 regarding the second action.

Thereafter, in the operation S400, the user terminal 100 may compare a completion status of each of the first, second, third, and fourth actions with a pre-stored reference operation value to determine a similarity therebetween.

At this point, the user terminal 100 may analyze the user's action by taking into consideration that the accelerometer sensor 250 and the microphone sensor 260 alternately and repeatedly detect the user's actions.

Specifically, the user terminal 100 may analyze the detection values over time by distinguishing the same based on a time when a relatively large detection value of the accelerometer sensor 250 occurs or when a relatively large detection value of the microphone sensor 260 occurs.

In the operation S400, the user terminal 100 may determine whether the first, second, third, and fourth actions have been performed. For example, a similarity may be determined by comparing the user's first, second, third, and fourth actions with an operation reference value.

Accordingly, the user terminal 100 may determine a similarity regarding each action to determine which of the user's first, second, third, and fourth actions has been completed and which action has not been completed, thereby enabled to determine a completion status for each individual action.

Thereafter, in the operation S500, the user terminal 100 may output result information regarding results of performing the first, second, third, and fourth actions. At this point, the user terminal 100 may output result information regarding each of the user's first, second, third, and fourth actions.

Therefore, for example, if it is determined that the user has failed to perform the fourth action of inhaling for 5 seconds with the button of the inhaler pressed and holding the breath for 10 second, the user terminal 100 fails to perform the fourth action and may output, in the form of a voice, a caution indicating that the effect of the treatment could be significantly reduced in this case.

In the operation S600, the user terminal 100 may transmit use information regarding the use of the healthcare device 10 to the server 300. For example, the user terminal 100 may transmit the use information to the server 300 by differentiating which of the first, second, third, and fourth actions have been performed and which action has not been performed.

Accordingly, after securing a sufficient storage capacity for the use information, the server 300 may analyze the user's habit or pattern for using the inhaler, determine which action during the user's usage of the inhaler primarily causes a problem, and transmit pattern information regarding the use of the inhaler to the user terminal 100.

In FIG. 5, an example has been described in which guide information regarding all actions of the user is output in the operation S100 while completion statuses of all of the actions of the user are determined in the operation S400 and result information is output in the operation S500; however, the present disclosure is not limited thereto, and the operation S100 to output guide information right before the start of performance of each action may be provided to output guide information regarding a following action, and the operation S400 immediately after the completion of each action and the operation S500 may be provided to determine a completion status of a previously performed action and output result information thereof.

For example, in FIG. 5, the operation S100 may be provided just before the operations S211, S212, S213, and S214, and the operation S400 and the operation S500 may be provided immediately after the operations S311, S312, S313, and S314.

The technical features disclosed in each embodiment of the present disclosure are not limited to the corresponding embodiment, and unless incompatible with each other, the technical features disclosed in each embodiment may be merged and applied to other embodiments.

Therefore, the embodiments are described mainly about the respective technical features, but the technical features may be merged and applied to each other unless incompatible with each other.

The present disclosure is not limited to the above-described embodiment and the accompanying drawings, and various modifications and changes may be made in view of the person skilled in the art to which the present disclosure pertains. The scope of the present disclosure should, therefore, be determined by equivalents to the claims, as well as by the claims of the present disclosure.

What is claimed is:

1. A method for guiding use of an inhaler, the method comprising:

receiving, by a user terminal, a detection value corresponding to a user-specific action of a user, from an auxiliary terminal worn on a body part of the user and configured to detect the user-specific action including at least one of a motion or a sound produced by the user during use of the inhaler, the auxiliary terminal being different and separate from the user terminal and configured to operate independently of the user terminal;

generating and storing, by the user terminal, in association with disease information, a reference operation value based on the detection value of the user specific action received from the auxiliary terminal, the reference operation value reflecting the user specific-action and varying according to an actual performance of the user;

receiving, by the user terminal, biometric information of the user from the auxiliary terminal, the biometric information including one or more of a pulse, an electrocardiogram, or a body temperature;

outputting, by the user terminal, the guide information regarding use of the inhaler when the biometric information of the user received from the auxiliary terminal satisfies a predetermined criterion, analyzing, by the user terminal, the detection value;

determining, by the user terminal, a completion status of the user specific action based on a similarity between the detection value and the reference operation value, wherein the similarity is evaluated by comparing the detection value with the reference operation value; and outputting, by the user terminal, result information indicating the completion status of the user specific action.

2. The method of claim 1, further comprising: after the determining of the completion status, transmitting, by the user terminal, use information regarding the use of the inhaler to a server.

3. The method of claim 1, wherein:

the auxiliary terminal comprises an accelerometer sensor and a microphone sensor, and the auxiliary terminal detects the user's action through at least one of the accelerometer sensor or the microphone sensor.

4. The method of claim 3, wherein:

the user's action comprises a plurality of actions, the guide information comprises guide information regarding all of the plurality of actions being output, and the detection value is received after the guide information regarding all of the plurality of actions is output, and detection values obtained by continuously detecting the plurality of actions by the auxiliary terminal are received from the auxiliary terminal.

5. The method of claim 4, wherein some of the plurality of actions are detected through the accelerometer sensor, and the remaining of the plurality of actions are detected through the microphone sensor.

6. The method of claim 5, wherein the plurality of actions comprise an action to be detected by the accelerometer sensor and an action to be detected through the microphone sensor alternately repeated.

7. The method of claim 6, wherein the analyzing is performed whenever the action detected by the accelerometer sensor is completed or the action detected by the microphone sensor is completed.

8. The method of claim 6, wherein the analyzing is performed after all of the plurality of actions of the user are completed.

9. The method of claim 1, wherein determining the completion status of the user's action comprises:

comparing the detection value and the reference operation value to determine the similarity between the detection value and the reference operation value; and determining that the user's action has been completed in response to the similarity satisfying a reference value.

10. A method for guiding use of an inhaler, the method comprising:

receiving, by a user terminal, a detection value corresponding to a user-specific action of a user, from an auxiliary terminal worn on a body part of the user and configured to detect the user-specific action including at least one of a motion or a sound produced by the user during use of the inhaler, the auxiliary terminal being different and separate from the user terminal and configured to operate independently of the user terminal;

generating and storing, by the user terminal, in association with disease information, a reference operation value based on the detection value of the user specific action received from the auxiliary terminal, the reference operation value reflecting the user specific-action and varying according to an actual performance of the user;

receiving, by the user terminal, biometric information of the user from the auxiliary terminal, the biometric information including one or more of a pulse, an electrocardiogram, or a body temperature of the user;

outputting, by the user terminal, guide information regarding use of the inhaler when the biometric information satisfies a predetermined criterion;

sequentially receiving, by the user terminal, from the auxiliary terminal, detection values respectively obtained by detecting a first action, a second action, a third action, and a fourth action of the user in association with the use of the inhaler, each action including at least one of motion or sound;

analyzing, by the user terminal, the detection values of the first to fourth actions, and determining completion statuses of the first to fourth actions based on the analysis; and outputting, by the user terminal, result information indicating the completion statuses of the first to fourth actions of the user, wherein the first action comprises opening a cap of the inhaler, the second action comprises exhaling by the user, the third action comprises holding the inhaler to the mouth and pressing a button of the inhaler, and the fourth action comprises inhaling for a first time period with the button of the inhaler being pressed and holding breath for a second time period longer than the first time period.

11. The method of claim 10, further comprising: after determining the completion statuses, transmitting, by the user terminal, use information regarding the use of the inhaler to a server.

12. The method of claim 10, wherein the outputting is performed before receiving the detection value obtained by detecting the first action, and guide information regarding all of the first to fourth actions is output.

13. The method of claim 10, wherein:

the outputting comprises outputting a plurality of sets of guide information, outputting each of the plurality of sets of guide information is performed immediately before receiving the first detection value obtained by detecting the first action, immediately before receiving the second detection value obtained by detecting the second action, immediately before receiving the third detection value obtained by detecting the third action, and immediately before receiving the fourth detection value obtained by detecting the fourth action, and outputting the plurality of sets of guide information comprises outputting guide information regarding each of the first to fourth actions, which is required in the receiving of the respective actions.

14. The method of claim 10, wherein the first time period is determined in a range of 3 seconds to 7 seconds, and the second time period is determined in a range of 8 seconds to 12 seconds.

15. The method of claim 10, wherein the first action further comprises shaking the inhaler a predetermined number of times.

16. The method of claim 10, wherein determining the completion statuses of the first, second, third, and fourth actions comprises:

comparing each of the first to fourth detection values and the reference operation value to determine the similarity between each of the first to fourth detection values and the reference operation value; and determining that one or more of the first to fourth actions have been completed in response to the similarity satisfying a reference value.

17. A user terminal for guiding use of an inhaler, the user terminal comprising:

a memory;

a processor connected to the memory and configured to execute instructions contained in the memory;

an output unit configured to output information under control of the processor; and a communication module configured to receive a detection value corresponding to a user-specific action of a user, from an auxiliary terminal worn on a body part of the user and configured to detect the user-specific action including at least one of a motion or a sound produced by the user during use of the inhaler, the auxiliary terminal being different and separate from the user terminal and configured to operate independently of the user terminal, wherein the processor is further configured to:

generate and store, in association with disease information, a reference operation value based on the detection value of the user specific action received from the auxiliary terminal, the reference operation value reflecting the user specific-action and varying according to an actual performance of the user;

perform a control to receive biometric information of the user from the auxiliary terminal, the biometric information including one or more of a pulse, an electrocardiogram, or a body temperature;

perform a control to output guide information regarding use of the inhaler when the biometric information satisfies a predetermined criterion;

sequentially receive detection values respectively obtained by detecting a first action, a second action, a third action, and a fourth action of the user in association with the use of the inhaler from the auxiliary terminal, each action including at least one of motion or sound, analyze the detection values, and determine completion statuses of the first to fourth actions based on the analysis; and perform a control to output result information indicating the completion statuses of the first to fourth actions of the user, wherein the first action comprises opening a cap of the inhaler, the second action comprises exhaling by the user, the third action comprises holding the inhaler to the mouth and pressing a button of the inhaler, and the fourth action comprises inhaling for a first time period with the button of the inhaler pressed and holding breath for a second time period longer than the first time period.

18. The user terminal of claim 17, wherein the user terminal outputs guide information regarding the action of the user before the auxiliary terminal detects the action of the user.

* * * * *